(12) United States Patent
Ghannad

(10) Patent No.: US 7,582,120 B2
(45) Date of Patent: Sep. 1, 2009

(54) COMPOSITION AND SYSTEM FOR HAIR COLORING AND COLOR RETENTION

(75) Inventor: Ali D. Ghannad, Woodlands, TX (US)

(73) Assignee: Farouk Systems, Inc., Houston, TX (US)

( * ) Notice: Subject to any disclaimer, the term of this patent is extended or adjusted under 35 U.S.C. 154(b) by 193 days.

(21) Appl. No.: 11/349,606

(22) Filed: Feb. 8, 2006

(65) Prior Publication Data

US 2007/0245502 A1 Oct. 25, 2007

Related U.S. Application Data

(60) Provisional application No. 60/651,282, filed on Feb. 9, 2005.

(51) Int. Cl.
*A61Q 5/06* (2006.01)
*A61Q 5/10* (2006.01)

(52) U.S. Cl. .................. 8/405; 8/552; 8/558; 424/70.6; 424/70.11; 424/70.12; 424/70.16

(58) Field of Classification Search ...... 8/405, 8/406; 424/70.6, 70.11, 70.12, 70.16
See application file for complete search history.

(56) References Cited

U.S. PATENT DOCUMENTS

| 5,061,481 | A | * | 10/1991 | Suzuki et al. | 424/63 |
| 5,658,557 | A | * | 8/1997 | Bolich et al. | 424/70.12 |
| 6,086,862 | A | | 7/2000 | Dubief et al. | |
| 6,090,376 | A | | 7/2000 | Dubief et al. | |
| 6,143,286 | A | * | 11/2000 | Bhambhani et al. | 424/70.1 |
| 6,471,952 | B1 | | 10/2002 | Dubief et al. | |
| 6,538,061 | B2 | * | 3/2003 | Chaiyawat et al. | 524/806 |
| 6,630,133 | B1 | | 10/2003 | Dupuis | |
| 2002/0053110 | A1 | * | 5/2002 | Dias et al. | 8/405 |
| 2004/0037796 | A1 | * | 2/2004 | Cottard et al. | 424/70.14 |
| 2004/0126346 | A1 | | 7/2004 | Martin et al. | |
| 2006/0029559 | A1 | * | 2/2006 | Tamura | 424/70.12 |

FOREIGN PATENT DOCUMENTS

WO 2004/058198 * 7/2004

OTHER PUBLICATIONS

CHI Brochure distributed in Cancun, Mexico with product samples, Aug. 26, 2004, 4 pages.
Grant Industries:[Online] 2004, XP002387409, http://www.grantinc.com/Personal_Care/Formulations/foundations/f-1256.htm, retrieved on Jun. 27, 2006, p. 1-2.
"Formulation Enhancement Through The Use of Gelled Emollients", by David S. Morrison, Ph.D. and Gina Butuc, Penreco Inc., Penreco Technology Center Publication, Woodlands, Texas, pp. 239-244, 1997.

* cited by examiner

*Primary Examiner*—Lorna M Douyon
*Assistant Examiner*—Amina Khan
(74) *Attorney, Agent, or Firm*—Greenberg Traurig, LLP

(57) ABSTRACT

A composition and system for use in coloring hair and improving color retention properties in colored hair are described. The composition of the present invention preferably includes hair dye and a copolymer of isobutylmethacrylate and silicone grafted acrylate in isoparaffin, whereby these components are combined in an aqueous based, or alternatively, a nonaqueous based solution. The system includes the step of applying the hair coloring solution to the hair.

22 Claims, No Drawings

COMPOSITION AND SYSTEM FOR HAIR COLORING AND COLOR RETENTION

RELATED APPLICATIONS

This nonprovisional patent application claims the benefit of provisional patent application U.S. Ser. No. 60/651,282, filed on Feb. 9, 2005, which is hereby incorporated by reference in its entirety.

BACKGROUND OF THE INVENTION

1. Field of the Invention

The present invention relates to the coloring of hair, and in particular to a composition and system for hair coloring that also protects the hair and prevents the fading of colored hair.

2. Description of the Related Art

Various compositions and formulations for hair coloring exist. The compositions include temporary hair colorings, which typically last until the first shampooing, semi-permanent hair colorings, which are generally resistant to several shampooings, and permanent hair colorings, which are resistant to shampooing for extended periods of time.

A disadvantage of these previous compositions and formulations, particularly the semi-permanent and permanent hair colorings, is that they often cause damage to the hair. Coloring of the hair involves the oxidizing of bonds in the hair structure, which can over-dry and weaken the hair structure, leaving the hair unhealthy and without shine. It would be advantageous to provide a hair coloring composition and system that, in addition to coloring the hair, also acts to protect and rejuvenate the hair to improve vibrancy and shininess.

Another disadvantage of these previous compositions and formulations for coloring hair is that they do not provide for improved color retention properties in colored hair. Some compositions have been used to prevent color from fading from colored hair. However, these compositions have been used in products such as shampoos, conditioners, hair serums and touch-up colorants, which are all applied to the hair only after it has been colored. It would be advantageous to provide a hair coloring composition and system that improves color retention properties in the hair at the same time as the hair is being initially colored.

Another disadvantage of these previous compositions and formulations for hair coloring is that they are difficult to use, in that they drip or bleed when the coloring is being applied to the hair, particularly when heat is applied to the hair. It would be advantageous to provide a hair coloring treatment that does not drip or bleed as it is applied to the hair.

Accordingly, prior to the development of the present invention, there has been no composition and system for hair coloring which: provided improved color retention properties in hair at the same time as the hair was being initially colored; was capable of improving the vibrancy and shininess of colored hair; reduced dripping or bleeding of the coloring, particularly under heat; and was economical and easy to apply and/or use. Therefore, the art has sought a composition and system for coloring of hair which: improves color retention properties in hair at the same time as the hair is being initially colored; is capable of improving the vibrancy and shininess of colored hair; reduces dripping or bleeding of the coloring, particularly under heat; and is economical and easy to apply and/or use.

SUMMARY OF THE INVENTION

In accordance with the invention, the foregoing advantages have been achieved through the present composition for use in coloring hair and improving color retention properties in colored hair. The composition of the present invention preferably includes hair dye and a copolymer of isobutylmethacrylate and silicone grafted acrylate in isoparaffin, whereby these components are combined in an aqueous based solution.

In accordance with another aspect of the invention, the foregoing advantages have also been achieved through the present composition for use in coloring hair and improving color retention properties in colored hair. This composition of the present invention may include hair dye and a copolymer of isobutylmethacrylate and silicone grafted acrylate in isoparaffin, whereby these components are combined in a non-aqueous based solution.

In accordance with yet another aspect of the invention, the foregoing advantages have also been achieved through the present system for use in coloring hair and improving color retention properties in colored hair. This aspect of the present invention may include the step of applying a hair coloring solution to the hair, whereby the solution includes hair dye and a copolymer of isobutylmethacrylate and silicone grafted acrylate in isoparaffin, and whereby these components are combined in a non-aqueous based solution.

In accordance with still another aspect of the invention, the foregoing advantages have also been achieved through the present system for use in coloring hair and improving color retention properties in colored hair. This aspect of the present invention may include the step of applying a hair coloring solution to the hair, whereby the solution includes hair dye and a copolymer of isobutylmethacrylate and silicone grafted acrylate in isoparaffin, and whereby these components are combined in an aqueous based solution.

The composition and system of the present invention, when compared with previously proposed compositions and systems for hair coloring, have the advantages of: improving color retention properties in hair at the same time as the hair is being initially colored; being capable of improving the vibrancy and shininess of colored hair; reducing dripping or bleeding of the coloring, particularly under heat; and being economical and easy to apply and/or use.

While the invention will be described in connection with the preferred embodiment, it will be understood that it is not intended to limit the invention to that embodiment. On the contrary, it is intended to cover all alternatives, modifications, and equivalents as may be included within the spirit and scope of the invention as defined by the appended claims.

DETAILED DESCRIPTION OF THE INVENTION

The present invention involves a hair coloring composition, and a system for using such a composition. The composition includes one or more hair dyes combined with a silicon acrylate copolymer. The system includes the step of using the composition in hair that is being colored, such that the hair strands are coated with the silicon acrylate copolymer. The silicon acrylate copolymer forms a film or coating on the hair strands, which protects the hair from damage by the colorant, improves color retention properties in the hair and reduces bleeding and dripping of the colorant.

In one embodiment, the hair colorant formulation of the present invention includes a copolymer of isobutylmethacrylate and silicone grafted acrylate in isoparaffin, which is produced and sold by Grant Industries, Inc., of Elmwood Park, N.J. under the product name "GRANACRYSIL™ BMAS" ("BMAS"). The INCI, or International Nomenclature of Cosmetics Ingredients, name for BMAS is Isododecane (and) Isobutylmethacrylate/Hydroxypropyl Dimethiconylpropyl Acrylates Copolymer, or alternatively, Isododecane (and) Isobutylmethacrylate/Bis-Hydroxypropyl Dimethicone Acrylate Copolymer. Other silicon copolymers can also be utilized in accordance with the present invention.

BMAS is a clear liquid copolymer in isoparaffin with a viscosity of about 1000-5000 cP and a non-volatile matter weight percentage of about 38.0-42.0%. A beneficial feature of BMAS is that it dries quickly when applied to the hair strands to form a clear, long lasting, glossy film that is breathable, flexible and exhibits strong adhesion and water repellency properties.

According to an embodiment of the present invention, as the hair is being colored, the silicon copolymer attaches to the hair strands and forms a thin coating over the strands. The silicon copolymer is preferably in the form of a gel. The coating traps the coloring on the hair, which advantageously reduces the amount of dripping or bleeding of color solution from the hair. In a preferred embodiment, the amount of bleeding is reduced by approximately 70-80%. The coating also makes the hair strands hydrophobic, and as a result the hair coloring cannot be rinsed out as easily after multiple washings, and the color does not fade as quickly. It has been discovered that the composition of the present invention allows the hair to retain and maintain its color for about two to six weeks, with a significant improvement in color maintenance properties after approximately twenty washes. Further, in a preferred embodiment, BMAS is a creme, and when it is added to the hair coloring it advantageously increases the viscosity of the coloring, which makes the coloring easier to apply to the hair and less likely to drip or bleed. The composition of the present invention also conditions and protects the hair and improves the vibrancy and shininess of the hair.

According to the present invention, the BMAS is combined with hair dye to form a hair colorant composition with improved properties. A preferred embodiment of the present invention includes the following approximate composition, on a weight basis:

| Material | Percentage (%) | Quantity (grams) |
| --- | --- | --- |
| Mineral Oil | 20.00 | 60.0 |
| Red #2 | 2.40 | 7.2 |
| Red #22 | 1.50 | 4.5 |
| BMAS | 4.00 | 12.0 |
| VERSAGEL ™ M 1600 | 13.00 | 39.0 |
| Lightening Powder | 59.10 | 177.0 |

The composition of the present invention may be utilized in either water-based or anhydrous, nonwater-based hair coloring systems. Anhydrous systems are utilized, for example, when chemicals which are reactive with water, such as potassium persulfate, are present in the hair coloring. According to an embodiment of the present invention, isododecane is utilized as a preferred solvent in an anhydrous system. Although a composition containing approximately 4.00 weight % BMAS is described as a preferred embodiment, it is to be noted that a composition containing in the range of approximately 0.1-10.0% BMAS may be utilized in accordance with the present invention. Further, the composition of the present invention can be utilized with temporary hair colorings, semi-permanent hair colorings and permanent hair colorings, and the BMAS can be combined with various types of dyes and hair colorings.

It is to be understood that the invention is not limited to the exact details of construction, operation, exact materials, or embodiment shown in described, as obvious modifications and equivalents will be apparent to one skilled in the art, or technological field. Accordingly, the invention is therefore to be limited only by the scope of the appended claims.

We claim:

1. A composition for use in coloring hair and retaining color in colored hair, the composition comprising: hair dye; and an isobutylmethacrylate and silicone grafted hydroxypropyl dimethiconylpropyl acrylate copolymer, whereby the hair dye and copolymer are combined in a non-aqueous based solution.

2. The composition of claim 1, wherein the hair dye is a temporary hair dye.

3. The composition of claim 1, wherein the hair dye is a permanent hair dye.

4. The composition of claim 1, wherein the copolymer comprises 0.1-10.0 weight percent of the composition.

5. The composition of claim 1, wherein the copolymer includes a gelled emollient which increases the viscosity of the composition.

6. The composition of claim 1, wherein the composition forms a coating over the strands of hair as the hair is being colored.

7. The composition of claim 1, wherein the non-aqueous based solution is isododecane.

8. The composition of claim 5, wherein the gelled emollient is transparent.

9. The composition of claim 1, wherein the composition contains isoparaffin.

10. A process for coloring hair comprising the steps of:
applying a hair coloring solution to the hair, the solution comprising the composition of claim 1;
forming a viscous coating over the strands of hair; and
trapping the hair dye from the hair coloring solution on the strands of hair with the coating to prevent dripping or bleeding of the hair dye from the hair.

11. A system for coloring hair, the system comprising the step of:
applying a hair coloring solution to the hair, the solution comprising the composition of claim 1, whereby the solution colors the hair and forms a coating over the strands of hair to trap the hair dye from the solution on the strands of hair and retain color in the hair.

12. A composition for use in coloring hair and retaining color in colored hair, the composition comprising: hair dye; and an isobutylmethacrylate and silicone grafted bishydroxypropyl dimethiconylpropyl acrylate copolymer, whereby the hair dye and copolymer are combined in a non-aqueous based solution.

13. The composition of claim 12, wherein the hair dye is a temporary hair dye.

14. The composition of claim 12, wherein the hair dye is a permanent hair dye.

15. The composition of claim 12, wherein the copolymer comprises 0.1-10.0 weight percent of the composition.

16. The composition of claim 12, wherein the copolymer includes a gelled emollient which increases the viscosity of the composition.

17. The composition of claim 12, wherein the composition forms a coating over the strands of hair as the hair is being colored.

18. The composition of claim 12, wherein the non-aqueous based solution is isododecane.

19. The composition of claim 16, wherein the gelled emollient is transparent.

20. The composition of claim 12, wherein the composition contains isoparaffin.

21. A process for coloring hair comprising the steps of:
applying a hair coloring solution to the hair, the solution comprising the composition of claim 12;
forming a viscous coating over the strands of hair; and
trapping the hair dye from the hair coloring solution on the strands of hair with the coating to prevent dripping or bleeding of the hair dye from the hair.

22. A system for coloring hair, the system comprising the step of: applying a hair coloring solution to the hair, the solution comprising the composition of claim 12, whereby the solution colors the hair and forms a coating over the strands of hair to trap the hair dye from the solution on the strands of hair and retain color in the hair.

* * * * *

UNITED STATES PATENT AND TRADEMARK OFFICE
CERTIFICATE OF CORRECTION

| | |
|---|---|
| PATENT NO. | : 7,582,120 B2 |
| APPLICATION NO. | : 11/349606 |
| DATED | : September 1, 2009 |
| INVENTOR(S) | : Ali D. Ghannad |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 398 days.

Signed and Sealed this

Fourteenth Day of September, 2010

David J. Kappos
*Director of the United States Patent and Trademark Office*